US006444676B1

(12) United States Patent
Pang et al.

(10) Patent No.: US 6,444,676 B1
(45) Date of Patent: Sep. 3, 2002

(54) USE OF PARP INHIBITORS IN THE TREATMENT OF GLAUCOMA

(76) Inventors: Iok-Hou Pang, 125 Starbridge La., Grand Prairie, TX (US) 75052; Abbot F. Clark, 5603 Rachel Ct., Arlington, TX (US) 76017

( * ) Notice: Subject to any disclaimer, the term of this patent is extended or adjusted under 35 U.S.C. 154(b) by 14 days.

(21) Appl. No.: 09/723,511

(22) Filed: Nov. 28, 2000

Related U.S. Application Data

(60) Provisional application No. 60/172,761, filed on Dec. 20, 1999.

(51) Int. Cl.[7] .............................................. A61K 31/495
(52) U.S. Cl. .................... 514/253.02; 514/912; 514/913
(58) Field of Search ........................... 514/253.05, 912, 514/913

(56) References Cited

U.S. PATENT DOCUMENTS

| 5,756,510 A | 5/1998 | Griffin et al. ................ 514/261 |
| RE36,397 E | 11/1999 | Zhang et al. ................ 514/309 |

OTHER PUBLICATIONS

Buja et al . . . , *Apoptosis and Necrosis: Basic Types and Mechanisms of Cell Death*, Arch Pathol Lab Med., vol. 117:1208–1214, 1993.
Bright et al., *Apoptosis: Programmed Cell Death in Health and Disease*, Bioscience Report, vol. 14: 67–81, 1994.
Raff et al., *Programmed Cell Death and the Control of Cell sUrvival: Lessons From the Nervous System*, Science, vol. 262:295–700, 1993.
Thompson, Craig B., *Apoptosis in the Pathogensis and Treatment of Disease*, Science, vol. 267:1456–1462, 1995.
Van Buskirk et al., *Glaucomatous Optic Neuropathy*, American Journal Ophthalmology, vol. 113:447–452, 1992.
Quigley et al., *Retinal Ganglion Cell Death in Experimental Glaucoma and After Axotomy Occurs by Apoptosis*, Investigative Ophthalmology & Visual Science, vol. 36(5):774–786, 1995.
Büchi, Ernst R., *Cell Death in the Rat Retina After a Pressure–Induced Ischemia–Reperfusion Insult: An Electron Microscopic Study. I. Ganglion Cell Layer and Inner Nuclear Layer*, Exp Eye Res, vol. 55:605–613, 1992.
Garcia–Valenzuela et al., *Programmed Cell Death of Retinal Ganglion Cells During Experimental Glaucoma*, Exp Eye Res, vol. 61:33–44, 1995.

Villegas–Perez et al., *Rapid and Protracted Phases of Retinal Ganglion Cell Loss Follows Axotomy in the Optic Nerve of Adult Rat*, Journal of Neurobiology, vol. 24(1):23–36, 1993.
Berkelaar et al., *Axotomy Results in Delayed Death and Apoptosis of Retinal Ganglion Cells in Adult Rats*, Journal of Neuroscience, vol. 14(7):4368–4374, 1994.
Garcia–Valenzuela et al., *Apoptosis in Adult Retinal Ganglion Cells After Axotomy*, Journal of Neurobiology, vol. 25:431–438, 1994.
Levin et al., *Apoptosis of Retinal Ganglion Cells in Anterior Ischemic Optic Neuropathy*, Arch Ophthalmol, vol. 114:488–491, 1996.
De Murcia et al., *Poly(ADP–ribose) Polymerase: Molecular Biological Aspects*, BioEssays, vol. 13, 455–462, 1991.
Cosi et al., *Poly(ADP–ribose) Polymerase (PARP) Revisited, A New Role For an Old Enzyme: PARP Involvement in Neurodegernation and PARP Inhibitors as Possible Neuroprotective Agents*, Annals NY Academy of Sciences, vol. 825:366–379, 1997.
Berger, Nathan A., *Symposium: Cellular Response to DNA Damage: The Role of Poly(ADP–Ribose)*, Radiation Research, vol. 101:4–15, 1985.
Wallis, et al., *Neuroprotection Against Nitric Oxide Injury With Inhibitors of ADP–Ribosylation*, Neuropharmacology Neurotoxicology, vol. 5(3):245–248, 1993.
Cosi et al., *Poly(ADP–ribose) Polymerase: Early Involvement in Glutamate–Induced Neurotoxicity in Cultured Cerebellar Granule Cells*, Journal Neuroscience Research, vol. 39:38–46, 1994.
Lam, Tim, T.,*The effect of 3–Aminobenzamide, an Inhibitor of Poly–ADP–Ribose Polymerase, on Ischemia/Reperfusion Damage in Rat Retinal*, Research Communications in Molecular Pathology and Pharmacology, vol. 95:241–252, 1997.
Banasik et al., *Specific Inhibitors of Poly(ADP–ribose) Synthetase and Mono(ADP–ribose) Transferase*, Journal of Biological Chemistry, vol. 267(3):1569–1575, 1992.
Schanraufstatter et al., *Oxidant Injury of Cells. DNA Strand–Breaks Activate Polyadenosine Diphosphate–Ribose Polymerase and Lead to Depletion of Nicotinamide Adenine Dinucleotide*, Journal Clinical Investigation, vol. 77:1312–1320, 1986.

Primary Examiner—Zohreh Fay
(74) Attorney, Agent, or Firm—Sally S. Yeager

(57) ABSTRACT

The invention provides pharmaceutical compositions containing PARP inhibitors and methods of using these compositions to prevent, treat or ameliorate glaucomatous retinopathy and/or optic neuropathy.

4 Claims, No Drawings

USE OF PARP INHIBITORS IN THE TREATMENT OF GLAUCOMA

This application claims priority from U.S. Provisional Application Ser. No. 60/172,761 filed Dec. 20, 1999. The present invention relates to the treatment of retinal and optic nerve disease and disorder. In particular, the present invention relates to the use of compositions containing poly(ADP-ribose) polymerase ("PARP") inhibitors to prevent, treat or ameliorate retinal and optic nerve pathology and disorder related to glaucoma.

BACKGROUND OF THE INVENTION

Apoptosis has been established as an important mechanism associated with neuronal cell loss in ocular conditions such as ischemia-reperfusion injury, glaucomatous neuropathy, retinal vessel occlusion and ocular neurodegenerative diseases including retinopathies and optic nerve neuropathies. Under normal conditions, apoptosis is a physiological cell death process of eliminating unwanted cells (programmed cell death) without the involvement of inflammation or necrosis. During apoptosis, cells exhibit a condensation of the cytoplasm, internucleosomal fragmentation of DNA, condensation of chromatin and nucleus (pyknosis), alteration of cell membrane morphology (blebbing), and disruption of cytoskeleton (cell shape changes). Such cellular events lead to the subsequent collapse of the cell into discrete vesicles with intact membranes (apoptotic bodies) and its eventual phagocytosis by neighboring phagocytic cells (Buja et al., *Apoptosis and necrosis: basic types and mechanisms of cell death.*, Arch Pathol Lab Med, volume 117, pages 1208–1214 (1993); Bright & Khar, *Apoptosis: programmed cell death in health and disease.*, Biosci Report, volume 14, pages 67–81 (1994)).

In addition to mediating naturally-occurring programmed cell death, apoptosis in neuronal tissues can also be induced by neurotransmitters (such as amino acid excitotoxicity), cytokines, toxins, ischemia, mechanical trauma or trophic factor withdrawal (Raff et al., *Programmed cell death and the control of cell survival: lessons from the nervous system.* Science, volume 262, pages 695–700 (1993); and Thompson. *Apoptosis in the pathogensis and treatment of disease.*, Science, volume 267, pages 1456–1462, (1995)).

Apoptosis has been shown to play a role in the death of retinal ganglion cells ("RGC") during experimental glaucoma. For example, in monkey eyes with experimental ocular hypertension, there are at least ten times more apoptotic RGC than in fellow control eyes (Van Buskirk & Cioffi, *Glaucomatous optic neuropathy.*, Am J Ophthalmol, volume 113, pages 447–452 (1992); and Quigley et al., *Retinal ganglion cell death in experimental glaucoma and after axotomy occurs by apoptosis.*, Invest Ophthalmol Vis Sci, volume 36, pages 774–786 (1995)). Elevated intraocular pressure ("IOP") in rats was shown to induce apoptosis of RGC (Büichi, *Cell death in the rat retina after a pressure-induced ischemia-reperfusion insult: an electron microscopic study. I. Ganglion cell layer and inner nuclear layer.*, Exp Eye Res, volume 55, pages 605–613 (1992); and Garcia-Valenzuela et al., *Programmed cell death of retinal ganglion cells during experimental glaucoma.*, Exp Eye Res, volume 61, pages 33–44 (1995)). Additionally, optic nerve transection (an experimental procedure designed to mimic certain aspects of glaucomatous retinopathy) in monkeys, rabbits and rats was shown to induce apoptosis in RGCs (Villegas-Perez et al., *Rapid and protracted phases of retinal ganglion cell loss follows axotomy in the optic nerve of adult rat. J Neurobiol*, volume 24, pages 23–36 (1993); Berkelaar et al., *Axotomy results in delayed death and apoptosis of retinal ganglion cells in adult rats.*, J Neurosci, volume 14, pages 4368–4374, (1994); Garcia-Valenzuela et al., *Apoptosis in adult retinal ganglion cells after axotomy.*, J Neurobiol, volume 25, pages 431–438 (1994); and Quigley et al., *Invest Ophthalmol Vis Sci*, volume 36, pages 774–786 (1995)). RGC apoptosis also occurs in accelerated retinal ischemic diseases. The retina of an individual suffering from anterior ischemic optic neuropathy was shown to have increased the number of apoptotic RGC (Levin & Louhab, *Apoptosis of retinal ganglion cells in anterior ischemic optic neuropathy.*, Arch Ophthalmol, volume 114, pages 488–491 (1996)). Taken together, these studies strongly suggest that apoptosis is the, or at least a major, mechanism of RGC death during glaucomatous neuropathy.

Poly (ADP-ribose) polymerase (PARP; also known as "poly(ADP-ribose) synthetase") is an enzyme with a molecular mass of 113 kDa (De Murcia et al., *Poly(ADP-ribose) polymerase: molecular biological aspects.*, BioEssays, volume 13, pages 455–462 (1991)). Though it binds to chromatin under physiological conditions, it has a higher affinity for DNA strand breaks. It uses the oxidized form of nicotinamide adenine dinucleotide ("NAD$^+$") as a substrate to synthesize ADP-ribose polymer and transfers the polymer onto other proteins ("poly ADP-ribosylation"). Many proteins can be modified by PARP, such as DNA ligases, DNA and RNA polymerases, endonucleases, histones, topoisomerases and PARP itself. Poly ADP-ribosylation of these proteins affects their activities; some are activated, yet most are inactivated (Cosi et al., *Poly (ADP-ribose) polymerase (PARP) revisited. A new role for an old enzyme: PARP involvement in neurodegeneration and PARP inhibitors as possible neuroprotective agents., Ann NY Acad Sci*, volume 825, pages 366–379 (1997)). PARP can be activated by activation of caspases and by DNA damage. It is hypothesized to be a suicidal mediator when massive DNA damage occurs in a cell. Even though its exact mechanism of action is unknown, some speculate that change in enzymatic activities of proteins modified by poly ADP-ribosylation leads to impairment in cell function and apoptosis; others suggest that PARP serves in a futile "ADP-ribose polymerization and hydrolysis" cycle, which leads to energy depletion and apoptosis (Berger, *Cellular response to DNA damage: the role of poly(ADP-ribose), Radioation Res*, volume 101, pages 4–15 (1985)).

PARP inhibitors, such as benzamide, 3-aminobenzamide, 3-aminophtalhydrazide and 1,5-dihydroxyisoquinoline have been shown to prevent neuronal apoptosis induced by various injuries including amino acid excitotoxicity (Wallis, et al., *Neuroprotection against nitric oxide injury with inhibitors of ADP-ribosylation.*, Neuropharm Neurotoxicol, volume 5, pages 245–248 (1993); Cosi et al., *Poly(ADP-ribose) polymerase: early involvement in glutamate-induced neurotoxicity in cultured cerebellar granule cells.*, J Neurosci Res, volume 39, pages 38–46 (1994); and Cosi et al., *Poly(ADP-ribose) polymerase (PARP) revisited. A new role for an old enzyme: PARP involvement in neurodegeneration and PARP inhibitors as possible neuroprotective agents.*, Ann NY Acad Sci, volume 825, pages 366–379 (1997)). 3-Aminobenzamide (at 3 mM or higher concentrations, administered via intracameral infusion) also has been shown to reduce ischemia/reperfusion damage and DNA fragmentation in rat retina (Lam, *The effect of 3-aminobenzamide, an inhibitor of poly-ADP-ribose polymerase, on ischemia/reperfusion damage in rat retinal*, Res Commun Mol Pathol Pharmacol, volume 95, pages 241–252 (1997)).

U.S. Pat. No. 5,756,510 (Griffin et al.) discloses benzamide analogs that inhibit PARP DNA repair enzymes, and potentially useful in potentiating the effects of cytotoxic drugs or radiotherapy in cancer therapy.

U.S. Pat. No. Re. 36,397 (Zhang et al.) discloses PARP inhibitors and their potential use in the prevention of neurotoxicity mediated through N-methyl-D-aspartate (NDMA) receptors, and in the treatment of vascular stroke and neuronal diseases such as Alzheimer's disease, Parkinson's disease and Huntington's disease.

Nowhere in the art, however, has it been disclosed or suggested to use of these compounds to prevent, treat or ameliorate glaucomatous retinopathy and optic neuropathy.

SUMMARY OF THE INVENTION

The present invention is directed to compositions and methods of preventing, treating or ameliorating retinopathies and optic nerve diseases and disorders related to glaucoma. In particular, the present invention is directed to compositions containing compounds that inhibit the activation of PARP or PARP activity and methods of using these compositions to prevent, treat or ameliorate diseases and disorders of the retina and optic nerve related to glaucoma.

While not intending to be bound by theory, the inventors believe that inhibition of PARP protects the retinal neurons and/or the optic nerve by inhibiting apoptosis initiated by the activation of this enzyme, as described above.

The PARP inhibitors may be administered by various means such as orally, parenterally, intraocularly or topically. Examples of various compositions useful for these various pharmaceutical applications are described herein. Since there is no currently accepted treatment of glaucomatous retinopathy and optic neuropathy, the use of PARP inhibitors provides a novel means to prevent or reduce retina and optic nerve damage related to glaucoma.

DETAILED DESCRIPTION OF THE INVENTION

The present invention is directed to compositions and methods of preventing, treating or ameliorating glaucomatous retinopathy and optic neuropathy. More specifically, the present invention is directed to compositions containing compounds that inhibit or retard the activity of PARP and methods of using these compositions to prevent or treat diseases and disorders of the retina and optic nerve resulting from glaucoma. As described above, PARP is an intracellular enzyme that uses $NAD^+$ as a substrate to cause poly ADP-ribosylation of proteins important for the normal functioning of cells. Such protein modification leads to the subsequent apoptosis and cell death. While not intending to be bound by any theory, the inventors believe that, due to PARP involvement in cell death following cellular stress, PARP is involved in retinopathy and/or optic neuropathy related to glaucoma. The inventors of the present invention also believe that PARP inhibitors have therapeutic value in the prevention or treatment of glaucomatous retinopathy and optic neuropathy. As used herein, "PARP inhibitors" refer to those compounds or agents that inhibit or retard the activation of, or enzymatic activity of, PARP; and "inhibition of PARP" refers to the inhibition or retardation of the activation of PARP, or its activity. As stated above, PARP is believed to be a critical factor involved in ocular neuronal response to glaucoma.

The compositions and methods of the present invention employ one or more PARP inhibitors in an amount effective to prevent, treat or ameliorate glaucomatous retinopathy and/or optic neuropathy. PARP inhibitors are known in the art and may also be elucidated using various techniques. Examples of PARP inhibitors include benzamide, 3-aminobenzamide, 4-aminobenzamide, 3-aminophtalhydrazide and 1,5-dihydroxyisoquinoline. Preferred PARP inhibitors include benzamide, 3-aminophtalhydrazide and 1,5-dihydroxyisoquinoline.

Inhibition of PARP may be effected by a number of approaches. A preferred method of the present invention is to employ specific inhibitors of PARP. For example, specific inhibitors of PARP, such as benzamide, 3-aminobenzamide, 4-aminobenzamide, 3-aminophtalhydrazide and 1,5-dihydroxyisoquinoline, may be used to inhibit apoptosis induced by PARP activity. U.S. Pat. No. 5,756,510 (Griffin et al.) discloses benzamide analogs having PARP inhibitory efficacy and those compounds may be used in the present invention methods and compositions; the entire contents of which are incorporated herein by reference. U.S. Pat. No. Re. 36,397 (Zhang et al.) discloses PARP inhibitors useful for vascular stroke and neurodegenerative disorders and those compounds may be used in the present invention methods and compositions; the entire contents of which are incorporated herein by reference. The use of PARP-specific inhibitors would allow the activation of non-PARP-regulated pathways that are necessary for normal functioning of tissues, while inhibiting apoptosis of retina and optic nerve at risk.

The PARP inhibitors of the present invention may also be determined by various assays described in the literature. The following publications teach various methods which may be employed to elucidate PARP inhibitors:

1) U.S. Pat. No. 5,756,510 (Griffin et al.);
2) Banasik et al. *Specific inhibitors of poly(ADP-ribose) synthetase and mono(ADP-ribose) transferase., J Biol Chem,* volume 267, pages 1569–1575 (1992); and
3) Schanraufstatter et al. *Oxidant injury of cells. DNA strand-breaks activate polyadenosine diphosphate-ribose polymerase and lead to depletion of nicotinamide adenine dinucleotide., J Clin Invest,* volume 77, pages 1312–1320 (1986); the entire contents of the foregoing literature references are incorporated herein by reference.

The compositions of the present invention comprise one or more PARP inhibitors and a pharmaceutically acceptable vehicle. As used herein, the term "pharmaceutically acceptable vehicle" refers to any formulation which is acceptable, i.e., safe and provides the appropriate delivery for the desired route of administration, of an effective amount of one or more PARP inhibitors. The compositions of the present invention may be administered in a variety of different ways including systemically (e.g., oral administration, intramuscular injection, subcutaneous injection, intravenous injection, transdermal administration and transmucosal administration), topically and by intraocular injection, intraocular perfusion, periocular injection or retrobulbar (sub-tenon) injection.

The exact dosage of the PARP inhibitor(s) will vary, but will be determined by skilled clinicians in the art. Various factors affecting the dosage amount include the actual disease to be treated, the severity of condition, the health of the patient, the potency and specific efficacy of the PARP inhibitor, and so on. The amount dosed, however, will be sufficiently effective to prevent, treat or ameliorate glaucomatous retinopathy and/or optic neuropathy; such an amount is referred herein as an "effective amount." In general, the daily dosage of PARP inhibitors will range between about 0.001 and 100 milligrams per kilogram body weight per day (mg/kg/day), and preferably between about 0.01 and 5.0 mg/kg/day.

The PARP inhibitors of the present invention may be contained in various types of ophthalmic compositions, in accordance with formulation techniques known to those skilled in the art. For example, the compounds may be included in solutions, suspensions and other dosage forms adapted for topical, intravitreal or intracameral use.

Aqueous compositions are generally preferred, based on ease of formulation and physiological compatibility. However, the PARP inhibitors of the present invention may also be readily incorporated into other types of compositions, such as suspensions and viscous or semi-viscous gels or other types of solid or semi-solid compositions for topical or retrobulbar injection. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Topical ophthalmic products are typically packaged in multi-dose form. Preservatives are thus required to prevent microbial contamination during use. Suitable preservatives include: benzalkonium chloride, chlorobutanol, methyl paraben, propyl paraben, phenylethyl alcohol, edetate disodium, sorbic acid, polyquaternium-1, or other agents known to those skilled in the art. Some of these preservatives, however, may be unsuitable for particular applications, (e.g., benzalkonium chloride may be unsuitable for intraocular injection). Such preservatives are typically employed at a level of from 0.001 to 1.0% weight/volume ("% w/v").

While at the present time there are no effective methods to effect back of the eye treatment of chronic conditions via topical administration, it is contemplated that such methods will be developed. If topical administration of PARP inhibitors becomes feasible, the dosage generally will range between about 1–2 two drops administered to the eye 1–4 times per day of a composition comprising 0.001 and 5% weight/volume ("w/v"), and preferably between 0.1 and 1% (w/v) of one or more PARP inhibitors. Solutions, suspensions, ointments, gels, jellies and other dosage forms adapted for topical administration are preferred. Additionally, PARP inhibitors may be delivered slowly, over time, to the afflicted tissue of the eye through the use of contact lenses. This regimen is generally performed by first soaking the lenses in a PARP inhibitor solution, and then applying the contact lenses to the eye for normal wear.

The compositions of the present invention are further illustrated in the following formulation examples, PARP inhibitors of the present invention are represented generically in the examples as "PARP Inhibitor."

EXAMPLE 1

A topical ophthalmic composition useful for treating glaucomatous retinopathy and/or optic neuropathy:

| Ingredient | Concentration (% w/v) |
|---|---|
| PARP Inhibitor | 0.1 |
| Dibasic Sodium Phosphate | 0.2 |

-continued

| Ingredient | Concentration (% w/v) |
|---|---|
| HPMC | 0.5 |
| Polysorbate 80 | 0.05 |
| Benzalkonium Chloride | 0.01 |
| Sodium Chloride | 0.75 |
| Edetate Disodium | 0.01 |
| NaOH/HCl | q.s., pH 7.4 |
| Purified Water | q.s. 100% |

EXAMPLE 2

A sterile intraocular injection solution useful for treating glaucomatous retinopathy and/or optic neuropathy:

| Ingredient | Concentration (% w/v) |
|---|---|
| PARP Inhibitor | 0.05–5.0 |
| Cremophor EL ® | 10 |
| Tromethamine | 0.12 |
| Mannitol | 4.6 |
| Disodium EDTA | 0.1 |
| Hydrochloric acid or sodium hydroxide | q.s., pH to 7.4 |
| Water for injection | q.s. 100% |

EXAMPLE 3

A tablet formulation suitable for oral administration, and useful for treating glaucomatous retinopathy and/or optic neuropathy:

| Ingredient | Amount per Tablet (mg) |
|---|---|
| PARP Inhibitor | 200 |
| Cornstarch | 50 |
| Lactose | 145 |
| Magnesium stearate | 5 |

EXAMPLE 4

An systemic injectable solution useful for treating glaucomatous retinopathy and/or optic neuropathy:

| Ingredient | Amount |
|---|---|
| PARP Inhibitor | 200 mg |
| 0.4 M KH$_2$PO$_4$ solution | 2 ml |
| 1 N KOH solution | q.s. to pH 7.0 |
| Water for injection | q.s. to 20 ml |

We claim:

1. A method for treating retinal or optic nerve disease or damage related to glaucoma, which comprises administering to a mammal a composition containing an effective amount of one or more PARP inhibitors in a pharmaceutically acceptable vehicle.

2. A method according to claim 1 wherein the PARP inhibitor is selected from the group consisting of benzamide, 3-aminobenzamide, 4-aminobenzamide, 3-aminophtalhydrazide, 1,5-dihydroxyisoquinoline and their pharmaceutically acceptable analogs.

3. A method according to claim 1 wherein the PARP inhibitor is benzamide.

4. A method according to claim 1, which further comprises administering the composition by intraocular injection, ocular topical application, intravenous injection, oral administration, intramuscular injection, intraperitoneal injection, transdermal application or transmucosal application.

* * * * *